(12) United States Patent
Schwab et al.

(10) Patent No.: US 12,708,325 B2
(45) Date of Patent: Aug. 18, 2026

(54) SYSTEMS, METHODS, AND DEVICES WITH SENSORS HAVING MULTIPLE DETECTION SIGNAL TYPES

(71) Applicant: GS-HealthMatrix, LLC, Los Angeles, CA (US)

(72) Inventors: Joseph Schwab, Los Angeles, CA (US); Amirhossein Yazdkhasti, Los Angeles, CA (US); Hamid Ghaednia, Los Angeles, CA (US)

(73) Assignee: GS-HEALTHMATRIX, LLC, Los Angeles, CA (US)

( * ) Notice: Subject to any disclaimer, the term of this patent is extended or adjusted under 35 U.S.C. 154(b) by 0 days.

(21) Appl. No.: 18/819,062

(22) Filed: Aug. 29, 2024

(65) Prior Publication Data

US 2025/0072756 A1 Mar. 6, 2025

Related U.S. Application Data

(60) Provisional application No. 63/579,627, filed on Aug. 30, 2023, provisional application No. 63/579,633, (Continued)

(51) Int. Cl.
*A61B 5/00* (2006.01)
*A61B 5/256* (2021.01)
(Continued)

(52) U.S. Cl.
CPC .......... *A61B 5/6831* (2013.01); *A61B 5/0093* (2013.01); *A61B 5/256* (2021.01); (Continued)

(58) Field of Classification Search
CPC ..... A61B 5/0077; A61B 5/256; A61B 5/6831; A61B 5/742; A61B 5/1126; A61B 5/0048;
(Continued)

(56) References Cited

U.S. PATENT DOCUMENTS 5,299,454 A 4/1994 Fuglewicz et al.
6,063,046 A 5/2000 Allum
(Continued)

FOREIGN PATENT DOCUMENTS

CA 2928972 3/2022
CN 114869345 A 8/2022
(Continued)

OTHER PUBLICATIONS

International Search Report and Written Opinion for PCT/US2024/044434 mailed Nov. 8, 2024 (Applicant—GS-HEALTHMATRIX, LLC) (11 Pages).
(Continued)

*Primary Examiner* — Boniface N Nganga
(74) *Attorney, Agent, or Firm* — NORTON ROSE FULBRIGHT US LLP

(57) ABSTRACT

Systems, methods, and devices include a multi-sensor scanning device for characterizing a health parameter. A scanning portion formed at an end of the multi-sensor scanning device includes a first sensor assembly. The first sensor assembly has a glass section forming a contact surface and/or one or more LEDs operable to provide electromagnetic waves to an interior of the glass section. The first sensor assembly also includes a light sensor directed at a transmission surface of the glass section. Additionally, the system includes a second sensor assembly involving one or more sensors directed at a same target area as the contact surface. Also, the one or more sensors of the second sensor assembly include an electrically conductive coating formed onto the contact surface and/or one or more electrical transducers deposed at least partly around the contact surface. The device can be a platform with a standing portion.

19 Claims, 14 Drawing Sheets

Related U.S. Application Data filed on Aug. 30, 2023, provisional application No. 63/579,640, filed on Aug. 30, 2023, provisional application No. 63/579,647, filed on Aug. 30, 2023, provisional application No. 63/579,663, filed on Aug. 30, 2023, provisional application No. 63/579,616, filed on Aug. 30, 2023, provisional application No. 63/579,605, filed on Aug. 30, 2023.

(51) Int. Cl.

| | |
|---|---|
| ***A61B 5/296*** | (2021.01) |
| ***A61B 5/395*** | (2021.01) |
| ***A61B 7/00*** | (2006.01) |
| ***A61N 1/04*** | (2006.01) |
| ***A61N 7/00*** | (2006.01) |

(52) U.S. Cl.

CPC .............. *A61B 5/296* (2021.01); *A61B 5/395* (2021.01); *A61B 5/4523* (2013.01); *A61B 5/6803* (2013.01); *A61B 5/6806* (2013.01); *A61B 7/006* (2013.01); *A61N 1/0484* (2013.01); *A61N 7/00* (2013.01); *A61B 2560/0468* (2013.01); *A61B 2562/0204* (2013.01); *A61B 2562/046* (2013.01); *A61B 2562/066* (2013.01); *A61B 2562/164* (2013.01); *A61N 2007/0078* (2013.01)

(58) Field of Classification Search

CPC ... A61B 5/0062; A61B 5/0064; A61B 5/0079; A61B 5/0093; A61B 5/0537; A61B 5/1036; A61B 5/1104; A61B 5/296; A61B 5/395; A61B 5/4023; A61B 5/4504; A61B 5/4523; A61B 5/6803; A61B 5/6806; A61B 5/6887; A61B 5/6895; A61B 5/7445; A61B 2560/0468; A61B 2560/0204; A61B 2560/0233; A61B 2560/0431; A61B 2530/0443; A61B 2560/0462; A61B 2560/0247; A61B 2560/046; A61B 2560/066; A61B 2560/164; A61B 7/006; A61B 9/005; A61B 2090/064; A61B 90/06; A61B 2017/00893; A61B 2017/00902; A61B 17/06166; A61B 17/064; A61B 17/7001; A61B 17/8625; A61B 17/80; G01B 11/24; G01N 21/55; H04R 225/67; A61F 2/32; A61F 2/481; A61F 2002/30667

See application file for complete search history.

(56) References Cited

U.S. PATENT DOCUMENTS

| | | | |
|---|---|---|---|
| 6,259,108 | B1 | 7/2001 | Antonelli et al. |
| 6,355,937 | B2 | 3/2002 | Antonelli et al. |
| 7,849,619 | B2 | 12/2010 | Mosher, Jr. et al. |
| 8,441,467 | B2 | 5/2013 | Han |
| 9,501,145 | B2 | 11/2016 | Poupyrev et al. |
| 9,524,424 | B2 | 12/2016 | Greene |
| 10,668,305 | B2 | 6/2020 | Cheatham, III et al. |
| 11,238,264 | B2 | 2/2022 | Reinhold et al. |
| 11,531,756 | B1 | 12/2022 | Raguin et al. |
| 2005/0265585 | A1 | 12/2005 | Rowe |
| 2007/0203435 | A1 | 8/2007 | Novak |
| 2008/0288200 | A1 | 11/2008 | Noble |
| 2009/0240170 | A1 | 9/2009 | Rowley et al. |
| 2009/0306484 | A1 | 12/2009 | Kurtz et al. |
| 2010/0007896 | A1 | 1/2010 | Fishbaine |
| 2012/0095283 | A1 | 4/2012 | Andersson et al. |
| 2012/0162081 | A1 | 6/2012 | Stark |
| 2012/0190989 | A1 | 7/2012 | Kaiser et al. |
| 2013/0109030 | A1 | 5/2013 | Hardeman et al. |
| 2013/0119237 | A1 | 5/2013 | Raguin et al. |
| 2013/0253387 | A1 | 9/2013 | Bonutti et al. |
| 2014/0121479 | A1 | 5/2014 | O'Connor et al. |
| 2014/0303508 | A1 | 10/2014 | Plotnik-Peleg et al. |
| 2015/0038812 | A1 | 2/2015 | Ayaz et al. |
| 2015/0042979 | A1 | 2/2015 | Chimmalgi et al. |
| 2015/0351690 | A1 | 12/2015 | Toth et al. |
| 2016/0038038 | A1 | 2/2016 | Kovacs |
| 2017/0156662 | A1 | 6/2017 | Goodall et al. |
| 2017/0157430 | A1 | 6/2017 | Cheatham, III et al. |
| 2017/0319096 | A1 | 11/2017 | Kaiser et al. |
| 2018/0018492 | A1 | 1/2018 | Vilenskii et al. |
| 2018/0242860 | A1 | 8/2018 | LeBoeuf et al. |
| 2018/0353365 | A1 | 12/2018 | Harry et al. |
| 2019/0080158 | A1 | 3/2019 | Roberson et al. |
| 2019/0105517 | A1 | 4/2019 | Tyler |
| 2019/0290198 | A1 | 9/2019 | Belson et al. |
| 2019/0346925 | A1 | 11/2019 | Daniels |
| 2020/0146397 | A1 | 5/2020 | Coupe et al. |
| 2020/0276438 | A1 | 9/2020 | Bouton et al. |
| 2021/0000590 | A1 | 1/2021 | Remenschneider et al. |
| 2021/0204877 | A1 | 7/2021 | Alizadeh-Meghrazi et al. |
| 2022/0016485 | A1 | 1/2022 | Bissonnette et al. |
| 2022/0054845 | A1 | 2/2022 | Volpe et al. |
| 2022/0071489 | A1 | 3/2022 | Aronoff-Spencer et al. |
| 2022/0207909 | A1 | 6/2022 | Raguin et al. |
| 2022/0412857 | A1 | 12/2022 | Fujisaki et al. |
| 2023/0157564 | A1 | 5/2023 | Zuckerman-Stark et al. |
| 2024/0237916 | A1 | 7/2024 | Ghaednia et al. |

FOREIGN PATENT DOCUMENTS

| | | | |
|---|---|---|---|
| CN | 111513692 | B | 8/2023 |
| KR | 10-1728723 | B1 | 4/2017 |
| WO | 2010054352 | A1 | 5/2010 |
| WO | 2016178907 | A1 | 11/2016 |
| WO | 2022/232676 | A1 | 11/2022 |
| WO | 2022/262669 | A1 | 12/2022 |
| WO | 2023/158304 | A1 | 8/2023 |

OTHER PUBLICATIONS

International Search Report and Written Opinion for PCT/US2024/044357 mailed Nov. 12, 2024 (Applicant—GS-HEALTHMATRIX, LLC) (11 Pages).

International Search Report and Written Opinion for PCT/US2024/044364 mailed Nov. 12, 2024 (Applicant—GS-HEALTHMATRIX, LLC) (14 Pages).

International Search Report and Written Opinion for PCT/US2024/044417 mailed Nov. 13, 2024 (Applicant—GS-HEALTHMATRIX, LLC) (11 Pages).

International Search Report and Written Opinion for PCT/US2024/044385 maild Nov. 14, 2024 (Applicant—GS-HEALTHMATRIX, LLC) (12 Pages).

International Search Report and Written Opinion for PCT/US2024/044342 mailed Nov. 15, 2024 (Applicant—GS-HEALTHMATRIX, LLC) (20 Pages).

International Search Report and Written Opinion for PCT/US2024/044404 dated Nov. 15, 2024 (Applicant—GS-HEALTHMATRIX, LLC) (11 Pages).

Busch, "Reflex Sensors for Telemedicine Applications" SUN Scholar, Mar. 2008, retrieved on [Nov. 3, 2024]. Retrieved from the internet <URL: https://scholar.sun.ac.za/items/93293378-49d9-4530-9bd7-2bc4ed615e6f > entire document.

Zhao. "Ultrasound beam steering with flattened acoustic metamaterial Luneburg lens" Applied Physics Letters; Article [online]. Feb. 18, 2020. [retrieved Oct. 16, 2024]. Retrieved from the Internet: https ://pubs.aip.org/aip/apl/article/116/7 /071902/38294/Ultrasound-beam-steering-with-flattened-acoustic.

Offutt. "Suppression and facilitation of auditory neurons through coordinated acoustic and midbrain stimulation: Investigating a deep brain stimulator for tinnitus" Journal of Neural Engineering; Article [online]. Dec. 2014 [retrieved Oct. 16, 2024]. Retrieved form the Internet: https://pmc.ncbi.nlm.nih.gov/articles/PMC4244264/pdf/nihms-637078.pdf.

(56) References Cited

OTHER PUBLICATIONS

Rupin et al. "Mimicking the cochlea with an active acoustic metamaterial" New Journal of Physics; Article [online]. Aug. 2019 [retrieved Oct. 16, 2024]. Retrieved form the Internet: https://iopscience. iop.org/article/10.1088/1367-2630/ab3d8f/pdf.

110
124
120
111
118
112
122
114
106
109
108
107
113
116
115
102
104
100

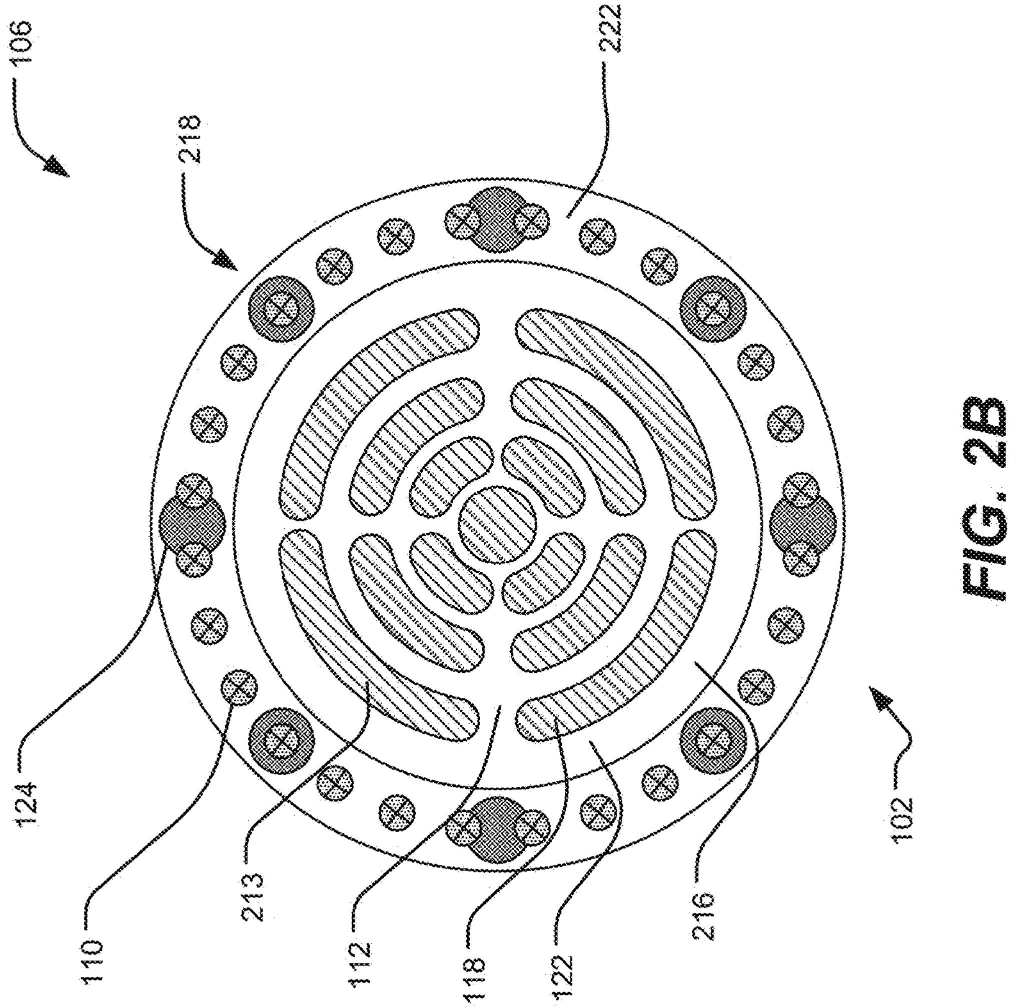
FIG. 2B

104
106
100
304
110
102

104
710
712
FS
106
714
708
100
122
112
110
120
102

SYSTEMS, METHODS, AND DEVICES WITH SENSORS HAVING MULTIPLE DETECTION SIGNAL TYPES

CROSS-REFERENCE TO RELATED APPLICATIONS

This application claims priority to U.S. Provisional Application Ser. No. 63/579,605 filed Aug. 30, 2023 and titled "FRUSTRATED TOTAL INTERNAL REFLECTION (FTIR) SURFACE TOPOGRAPHY AND COMPOSITION ANALYSIS SYSTEMS, METHODS, AND DEVICES;" U.S. Provisional Application Ser. No. 63/579,616 filed Aug. 30, 2023 and titled "SYSTEMS, METHODS, AND DEVICES OF WEARABLE ELECTRO-ACOUSTIC MONITORING;" U.S. Provisional Application Ser. No. 63/579,627 filed Aug. 30, 2023 and titled "SYSTEMS, METHODS, AND DEVICES FOR ACOUSTICALLY ENHANCING IMPLANTS;" U.S. Provisional Application Ser. No. 63/579,633 filed Aug. 30, 2023 and titled SYSTEMS, METHODS, AND DEVICES WITH SENSORS HAVING MULTIPLE DETECTION SIGNAL TYPES;" U.S. Provisional Application Ser. No. 63/579,640 filed Aug. 30, 2023 and titled MULTI-DEVICE HEALTH PARAMETER MONITORING SYSTEMS, METHODS, AND DEVICES;" U.S. Provisional Application Ser. No. 63/579,647 filed Aug. 30, 2023 and titled FRUSTRATED TOTAL INTERNAL REFLECTION (FTIR)-BASED HEALTH PARAMETER DETECTION SYSTEMS, METHODS, AND DEVICES;" and U.S. Provisional Application Ser. No. 63/579,663 filed Aug. 30, 2023 and titled "SYSTEMS, METHODS, AND DEVICES FOR NEUROLOGICAL AND/OR MUSCOSKELETAL PARAMETER CHARACTERIZATION;" the entireties of which are herein incorporated by reference.

BACKGROUND

A wide array of techniques exist for characterizing the human body for medical diagnoses and treatments. Computerized tomography (CT) scans, magnetic resonance imaging (MRI) and X-ray are commonly used. However, these systems are bulky, expensive, slow, and difficult to operate. Some smaller-scale devices for characterizing health-related parameters of the human body use electrodes disposed in a cuff. However, these types of devices are limited in the type of data they can collect. They also typically generate noise which prevents adoption for a wide range of different uses.

It is with these observations in mind, among others, that various aspects of the present disclosure were conceived and developed.

SUMMARY

Systems, methods, and devices disclosed herein can address the aforementioned issues. For instance, a multi-sensor scanning device for characterizing a health parameter can include a scanning portion formed at an end of the multi-sensor scanning device. The scanning portion can include a first sensor assembly having a glass section forming a contact surface; one or more light emitting diodes (LED) s operable to provide electromagnetic waves to an interior of the glass section; and/or a light sensor directed at a transmission surface of the glass section; and/or a second sensor assembly including one or more sensors directed at a same target area as the contact surface, the one or more sensors being a different type of sensor than the first sensor assembly; and/or a mounting portion at least partially housing one or more components of the scanning portion.

In some examples, the one or more sensors of the second sensor assembly can include an electrically conductive coating formed onto the contact surface. Moreover, the one or more sensors of the second sensor assembly can include one or more electrical transducers deposed at least partly around the contact surface. Additionally, the one or more sensors of the second sensor assembly can include one or more acoustic actuators or one or more acoustic sensors disposed at least partly around the contact surface. The one or more sensors of the second sensor assembly can include one or more force sensors communicatively coupled to the glass section such that the one or more force sensors are operable to detect a force applied to the contact surface of the glass section. The device can include a spring-loaded dampening system at the scanning portion of the multi-sensor scanning device. The light sensor can be operable to detect scattered light, originating from the one or more electromagnetic wave emitters, and scattered by frustrated total internal reflection (FTIR) occurring at the contact surface. Furthermore, the multi-sensor scanning device can be a handheld device; and/or the mounting portion can include a handle portion of the handheld device. The multi-sensor scanning device can also include a standing platform; and/or the mounting portion can include a base of the standing platform. The multi-sensor scanning device can be a wearable device; and/or the mounting portion can include a strap of the wearable device.

In some scenarios, a system for characterizing a health parameter using multiple sensor types can include a scanning portion formed at an end of a scanning device. The scanning portion can include a first sensor assembly having a transparent section forming a contact surface. The scanning portion can also include one or more electromagnetic wave emitters operable to provide electromagnetic waves to an interior of the transparent section; and/or a light sensor and/or camera directed at the transparent section, the light sensor, and/or the camera can be operable to detect scattered light transmitting through the transparent section caused by frustrated total internal reflection (FTIR) occurring at the contact surface; and/or a second sensor assembly including one or more electrical sensors directed at a same target area as the contact surface.

In some instances, the one or more electrical sensors can include at least one of a transparent, electrically conductive ink disposed on the contact surface; and/or one or more electrodes disposed at least partly around the contact surface. The light sensor can be a visible light camera. Also, the second sensor assembly can be integrally formed into the scanning portion of the scanning device. The second sensor assembly, additionally or alternatively, can be a remote sensor assembly separate from the scanning portion of the scanning device.

Furthermore, the second sensor assembly can include a wearable device. The wearable device can include a third sensor assembly having at least one of an acoustic actuator or an acoustic sensor. Additionally, the third sensor assembly can include one or more acoustic actuators, or one or more acoustic transducers, directed at the same target area as the contact surface.

In some examples, a method for characterizing a health parameter using multiple sensor types can include collecting a first type of data using a first sensor assembly. The first sensor assembly can have a glass section forming a contact surface; one or more LEDs operable to provide electromagnetic waves to an interior of the glass section; and/or a light sensor directed at the glass section, the light sensor operable to detect scattered light transmitting through the glass section caused by frustrated total internal reflection (FTIR) occurring at the contact surface. The method can also include collecting a second type of data using a second sensor assembly, the second sensor assembly having one or more electrical sensors or one or more electrical actuators. The method can also include collecting a third type of data using a third sensor assembly, the third sensor assembly having one or more acoustic sensors or one or more acoustic actuators. The method can include generating a health parameter characterization using at least two of the first type of data, the second type of data, or the third type of data; and/or causing a display to present a visual indication of the health parameter characterization. Additionally, the first sensor assembly, the second sensor assembly, and/or the third sensor assembly can be formed into a scanning portion of a handheld scanning device.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the disclosed subject matter. It should be understood, however, that the disclosed subject matter is not limited to the precise embodiments and features shown. The accompanying drawings, which are incorporated in and constitute a part of this specification, illustrate an implementation of systems and methods consistent with the disclosed subject matter and, together with the description, serves to explain advantages and principles consistent with the disclosed subject matter, in which:

FIGS. 2A and 2B illustrate an example system for characterizing a health parameter with a multi-signal scanning device having a handheld form factor.

DETAILED DESCRIPTION

Figure 1:
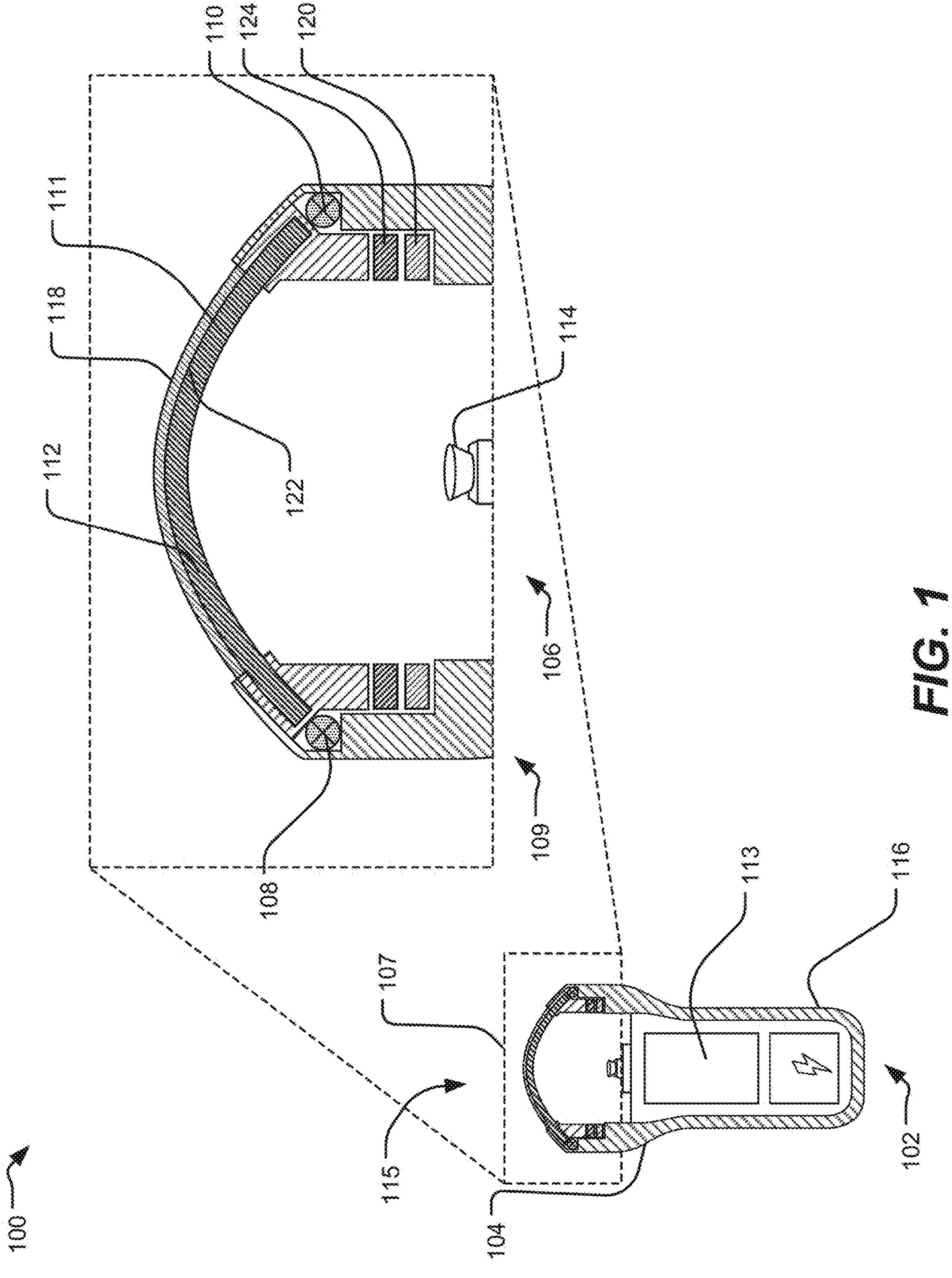
FIG. 1 illustrates an example system for characterizing a health parameter with a multi-signal scanning device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the presently disclosed technology or the appended claims. Further, it should be understood that any one of the features of the presently disclosed technology may be used separately or in combination with other features. Other systems, methods, features, and advantages of the presently disclosed technology will be, or become, apparent to one with skill in the art upon examination of the figures and the detailed description. It is intended that all such additional systems, methods, features, and advantages be included within this description, be within the scope of the presently disclosed technology, and be protected by the accompanying claims.

Further, as the presently disclosed technology is susceptible to embodiments of many different forms, it is intended that the present disclosure be considered as an example of the principles of the presently disclosed technology and not intended to limit the presently disclosed technology to the specific embodiments shown and described. Any one of the features of the presently disclosed technology may be used separately or in combination with any other feature. References to the terms "embodiment," "example," and/or the like in the description mean that the feature and/or features being referred to are included in, at least, one aspect of the description. Separate references to the terms "embodiment," "examples," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the presently disclosed technology may include a variety of combinations and/or integrations of the examples described herein. Additionally, all aspects of the present disclosure, as described herein, are not essential for its practice. Likewise, other systems, methods, features, and advantages of the presently disclosed technology will be, or become, apparent to one with skill in the art upon examination of the figures and the description. It is intended that all such additional systems, methods, features, and advantages be included within this description, be within the scope of the presently disclosed technology, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B, or C" or "A, B, and/or C" mean any of the following: "A," "B," or "C"; "A and B"; "A and C"; "B and C"; "A, B and C." An exception to this definition will occur only when a combination of elements, functions, steps or acts are in some way inherently mutually exclusive.

The systems, methods, and devices disclosed herein include a sensor device that can integrate two, three, four, or five measurement/actuation types of signals, including at least: electrical, acoustic, optical, thermal, and/or force. This disclosed device can provide one of the most comprehensive sets of simultaneously acquired signals. The techniques performed using multiple signals can result in a new understanding of the human body that can improve the screening, diagnosis, treatment and prevention of disease.

The different modalities of data signals (e.g., electrical, acoustic, optical, thermal, and/or force) have certain effects on each other. Meaning that for example, the device can generate and transmit acoustic waves on a living object such as human body, which can alter the electrical, optical, and/or electric properties of the body in one or more ways that can be measured and analyzed. Therefore, having two, three, four or even five modalities at a same place and communicating with each other simultaneously can develop significant opportunities for development of diagnostic, therapeutic, and prevention devices in healthcare, agriculture, structural health monitoring, and animal health. Some examples can use up to three modalities of data signals: electrical acoustic, and/or optical). Additional examples can include a fourth modality of thermal, which can also use a same sensor/actuator assembly as the optical modality. For instance, infrared lights as well as visible and UV lights, can be used to thermally affect the medium and analyze the electro-opto-acoustic properties of the thermal input to the target area. Furthermore a fifth modality can include force measurements, which can be used to normalize measurements of the other modalities. Moreover, the devices disclosed herein can be designed in different scales and can be used as a single-purpose measurement tool, a single sensor modality measurement tool, a multiple-purpose measurement tool, and/or a multiple sensor tool using multiple different types of sensors of different modalities.

The technology disclosed herein can be used in several different types of procedures and use cases, such as muscle monitoring while simultaneously analyzing body composition; monitoring and treatment of a diabetic foot; plant health monitoring; endoscopy, arthroscope or laparoscopic probes for non-invasive diagnosis; and/or combinations thereof.

Additional advantages of the systems, methods, and devices discussed herein will become apparent from the detailed description below.

FIG. 1 illustrates an example system 100 including a sensor device 102 with one or more detection signal types for different sensor modalities. The sensor device 102 can be a multi-detection signal scanning device 104 that uses any combination of two, three, four, or five signal modalities (e.g., electrical, acoustic, optical, thermal, and/or force).

The system sensor device 102 can include a scanning portion 106 formed at one end 107. The scanning portion 106 can have a first sensor assembly 109, which can include a frustrated total internal reflection (FTIR)-based optical sensor assembly 108, or another type of optical sensor assembly. For instance, the sensor device 102 can use the concept of FTIR to trap electromagnetic waves (e.g., from one or more LEDs 110) inside a transparent medium 111 (e.g., a glass portion 112). The word transparent can be applied to the use of visible light as well as infrared light and/or ultraviolet light. In these cases, the transparent medium 111 can be a medium that does not filter or absorb any of the aforementioned electromagnetic waves. When the electromagnetic waves are trapped in the medium 111, this can create an environment to analyze the mechanical properties, the geometrical properties, and/or the chemical composition of any objects that come into contact with the transparent medium. These parameters of the object can be investigated using a camera 114 sensitive to the wavelength of the trapped light, or a light sensor that could be made from several different materials such as graphene.

Figure 3:
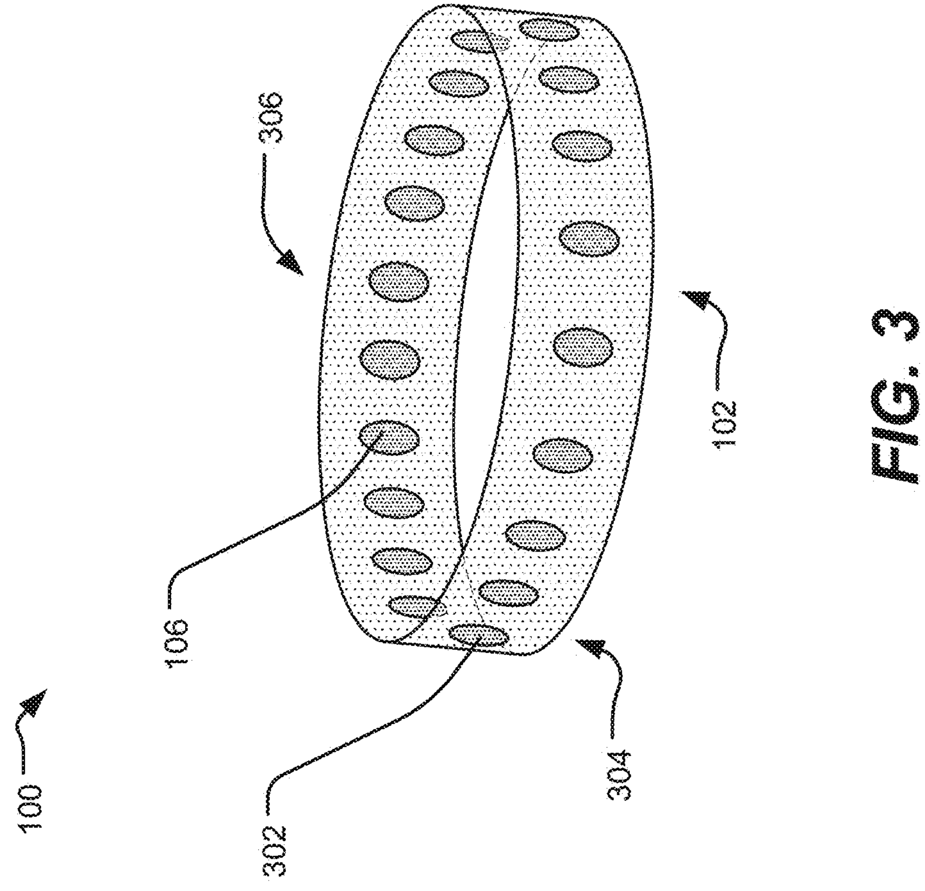
FIG. 3 illustrates an example system for characterizing a health parameter with a multi-signal scanning device having a cuff form factor.
Figure 9:
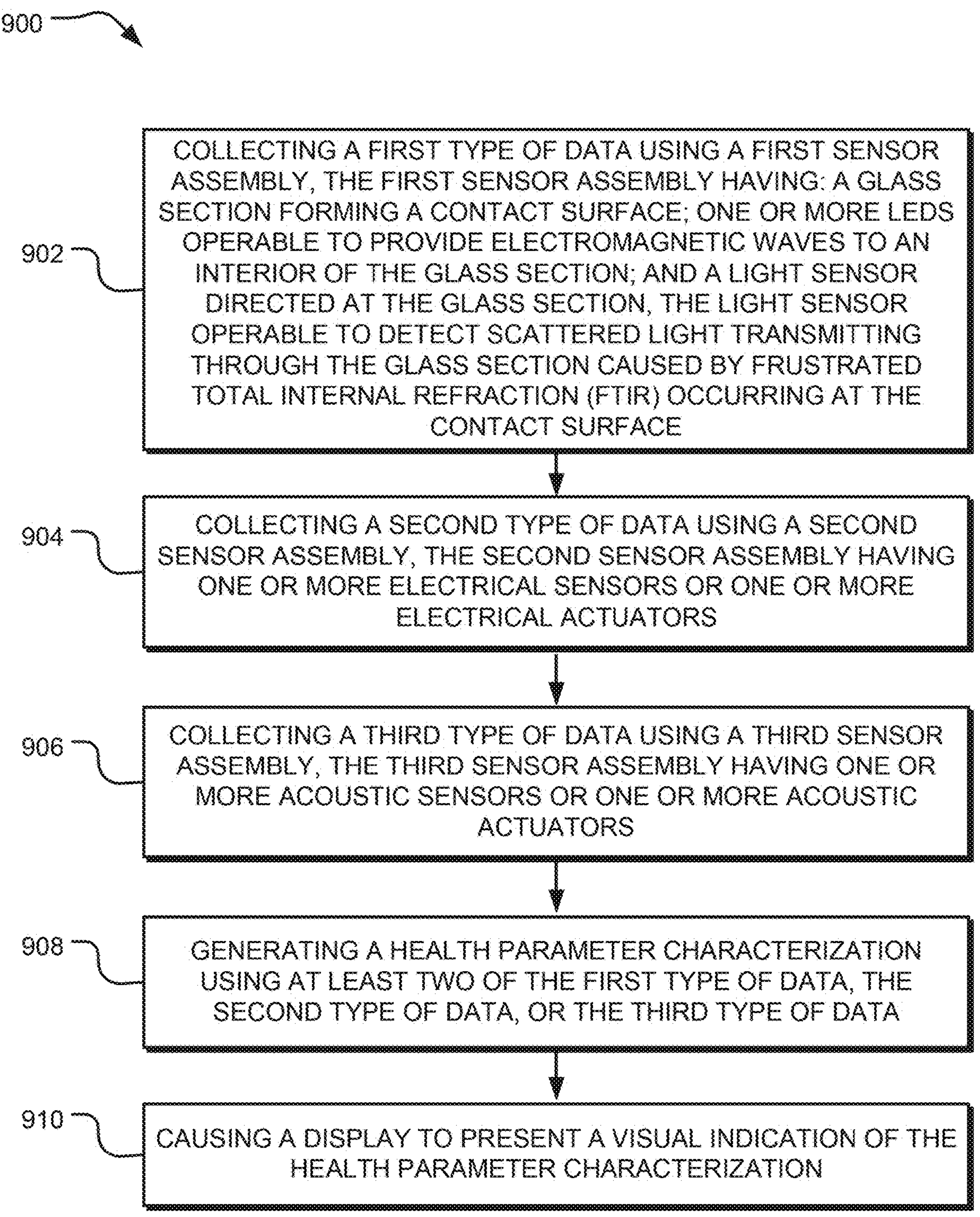
FIG. 9 depicts an example method for characterizing a health parameter with a multi-signal scanning device, which can be performed by any of the systems 1-8 disclosed herein.

The data 113 generated and collected with the first, optical modality can be combined with acoustic and electrical transducers and sensors (e.g., second and third modalities) to create a more comprehensive understanding of the contacting objects. In one application, as shown in FIG. 3 multiple sensors 302 can be put together in shape of a cuff 304 that covers part of human body such as arm. Then the acoustic and electrical waves could be used for muscle monitoring, and optical waves to analyze hydration level. The optical signal or FTIR signal can be used to measure a surface (e.g., roughness, friction value), pressure, and/or temperature of the contact surface of the sample. These three modalities (e.g., or four including thermal) can work simultaneously yet independently to inform one to four independent data analysis engines. The data analysis engines can generate outputs along two to four concurrent yet separate data analysis channels. without the data channels informing each other. In another application, this technology can be used with the different data analytics channels informing each other, both to generate cross-domain outputs, and to generate cross-domain actuation signals for further tissue stimulation and analysis, as shown in FIG. 9. For example, a cuff 304 including the multi-detection signal sensor assembly 115 can investigate the cardiovascular performance by applying acoustic stimulation to the target tissue and analyzing cardiovascular performance characteristics with the optical sensor. In this example, the optical measurements can be affected and informed by the acoustic or electrical stimulations.

The multi-detection signal scanning device 104 can include a glass surface 112 covered with or without an electrically conductive transparent ink/paint 118. The glass surface (e.g., glass portion 104) can trap light waves (e.g., visible, infrared, ultraviolet). This light-trapping glass system can sit on one or more acoustic transducers 118 which can, in turn, be sitting on one more force sensors 120. The force sensors 120 can collect force data, which can be correlated to other collected/transmitted signals (e.g., electrical, acoustic, optical, and/or thermal) to normalize the collected/transmitted signals. Furthermore, the acoustic transducer data can also be used to normalize the data (e.g., determine force or applied pressure value to be used for data normalization). Furthermore, the force sensor 120 can be omitted from the multi-signal sensor device. Various form factors and configurations of these components of the multi-detection signal scanning device 104 are discussed in greater detail below.

Figure 2A:
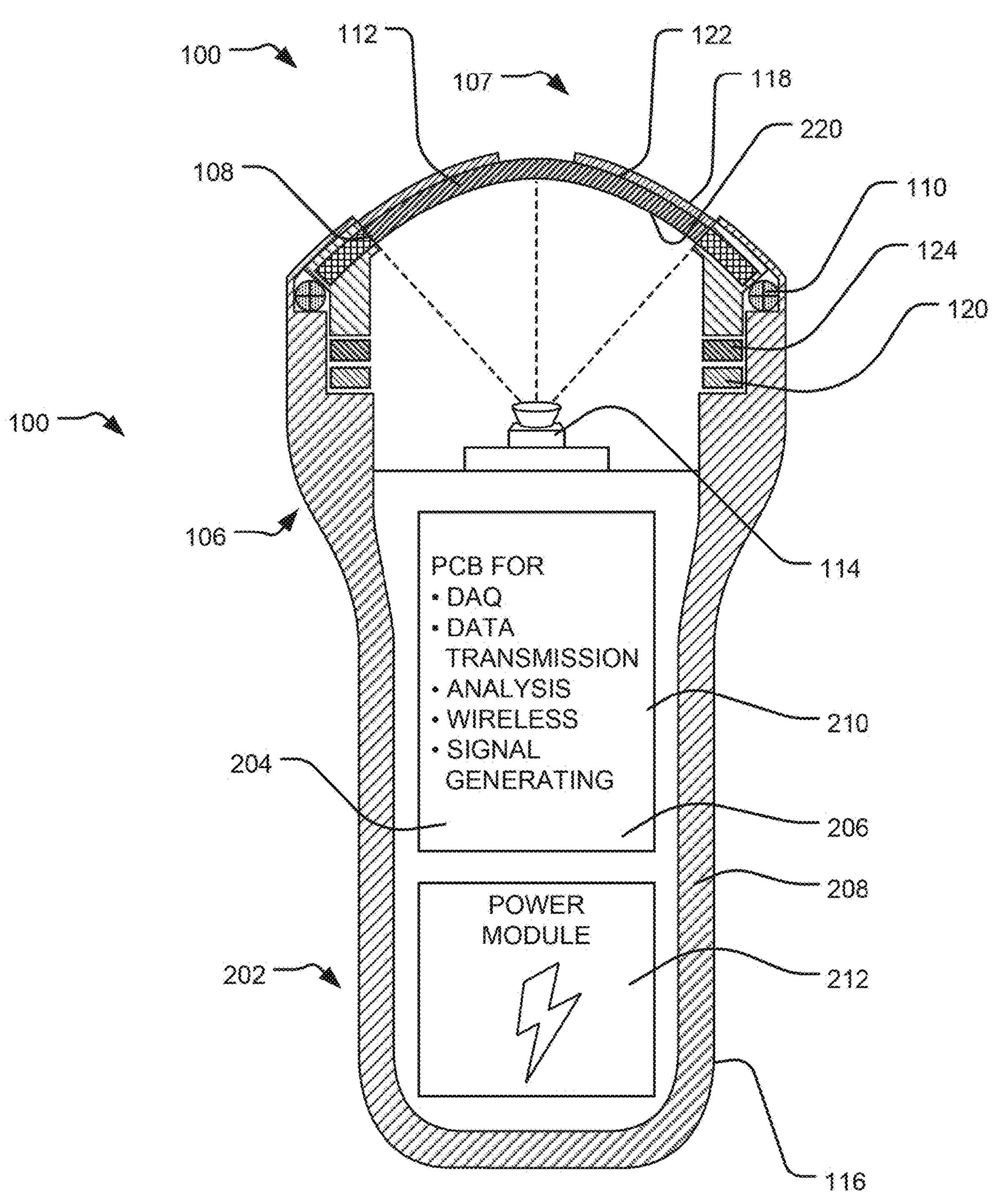

FIGS. 2A and 2B depict additional details of the multi-detection signal scanning device 104. As depicted in FIGS. 2A and 2B, the device 104 can be a handheld, multi-domain sensor capable of sensing and producing acoustic signals, electrical signals, optical signals, and/or thermal signals simultaneously.

In some examples, the multi-detection signal device 104 can have the scanning portion 106 (e.g., a detection head portion) at a first distal end 107 and a handle portion 116 at a second distal end 202 opposite the first distal end 107. The multi-detection signal scanning device 104 can include additional internal components 204 disposed in the handle portion 116. For instance, a PCB 206 can be at least partially enclosed by a housing 208 of the multi-detection signal scanning device 104 (e.g., in an internal cavity 210 of the multi-detection signal scanning device 104) and can include a data acquisition unit, a data transmission/receiver unit, an analysis unit, a wireless communication unit, and/or one or more signal generator units corresponding to the different detection signal modalities, and/or combinations thereof. Moreover, a power module 212 (e.g., battery, AV adapter, etc.) can also be formed into the multi-detection signal sensor device, for instance, at the handle portion 116.

Additionally, as depicted in FIG. 2B, electrical electrodes 214 can be printed in any shape or number on the glass surface 112 (e.g., a top surface 216 of the device 104). For instance, the glass surface 112 may have a circular profile 218, and the electrodes can be painted in solid circles, concentric circles, partial circle sections, curves, grids, rows, columns, arrays, or so forth. The multi-detection signal scanning device 104 can also include a light sensor or camera 114 to read light values from a detection side 220 of the glass sheet 112 opposite the contact surface 122 of the glass sheet 112. The light values can be caused by a frustrated total internal reflection (FTIR) event occurring at a contact 122 surface of the glass portion 112. For instance, the light sensor or camera 114 can be disposed in a cavity 210 in the detection head portion/handle portion of the device 102 facing a back surface of the glass portion 112 opposite the exposed contact surface 122. The multi-detection signal scanning device 104 can also include one or more acoustic transducers 124 capable of transmitting acoustic waves in different ranges, which can be disposed around a perimeter (e.g., a circumference) 222 or outer rim or edge of the contact surface 122 (e.g., glass portion 112). Additionally or alternatively, the multi-detection signal scanning device 104 can include one or more LEDs 110 disposed at least partly, or fully and/or evenly distributed around the contact surface 122 (e.g., to provide light into an interior of the glass portion 112. In some examples, the one or more LEDs 110 include a plurality of LEDs having different wavelengths corresponding to different detection parameters of the multi-detection signal scanning device 104. For instance, a particular set of LED frequencies can correspond to one or more molecules or compounds being detected with the analysis of FTIR-signals generated at the contact surface. Furthermore, the plurality of LEDs 110 can correspond to a particular set of contact distances for a 3D topology generated by the scattered FTIR photons and detected by the light sensor (e.g., the camera 114). In other words, each frequency of wavelength (e.g., between 10 nm and 4000 nm) can correspond to the distance from the contact surface at which an internal photon in glass portion 112 scatters. As such, by illuminating LEDs with different frequencies one-by-one, and aggregating the plurality of different frequency images together, the multi-detection signal scanning device 104 can generate a 3D-nanoscale map of the surface of the sample contacting the glass portion 112.

FIG. 3 depicts an example cuff 304 made of multiple electrodes 302 that can be used for muscle monitoring and/or skin condition monitoring. In some scenarios, the multi-sensor arrangement 306 of the multi-detection signal scanning device 104 can be made in different scales, such as a millimeter scale or centimeter scale), which can be formed into milli scale or cento scale multi-detection sensor nodes forming one or more rows or arrays on wearable technology. For instance, FIG. 3 depicts a cuff 302 made of multiple sensors 304 which can be used for muscle monitoring and/or skin condition monitoring in the mm and/or cm scale. Additionally, small scale versions of the disclosed technology can be used at the end of an endoscopy and/or GI probes. The multi-sensor arrangement 306 can also be formed in a larger scale (e.g., a centimeter scale and/or a meter scale), such as the handheld probe form-factor depicted in FIGS. 1-2B. Moreover, the multi-sensor arrangement 306 can be formed in a large-scale form-factor (e.g., a meter scale between 0.1 m and 100 m), such as a standing device or standing surface, a bed, a chair, a countertop, an exercise track, or so forth.

Figure 4:
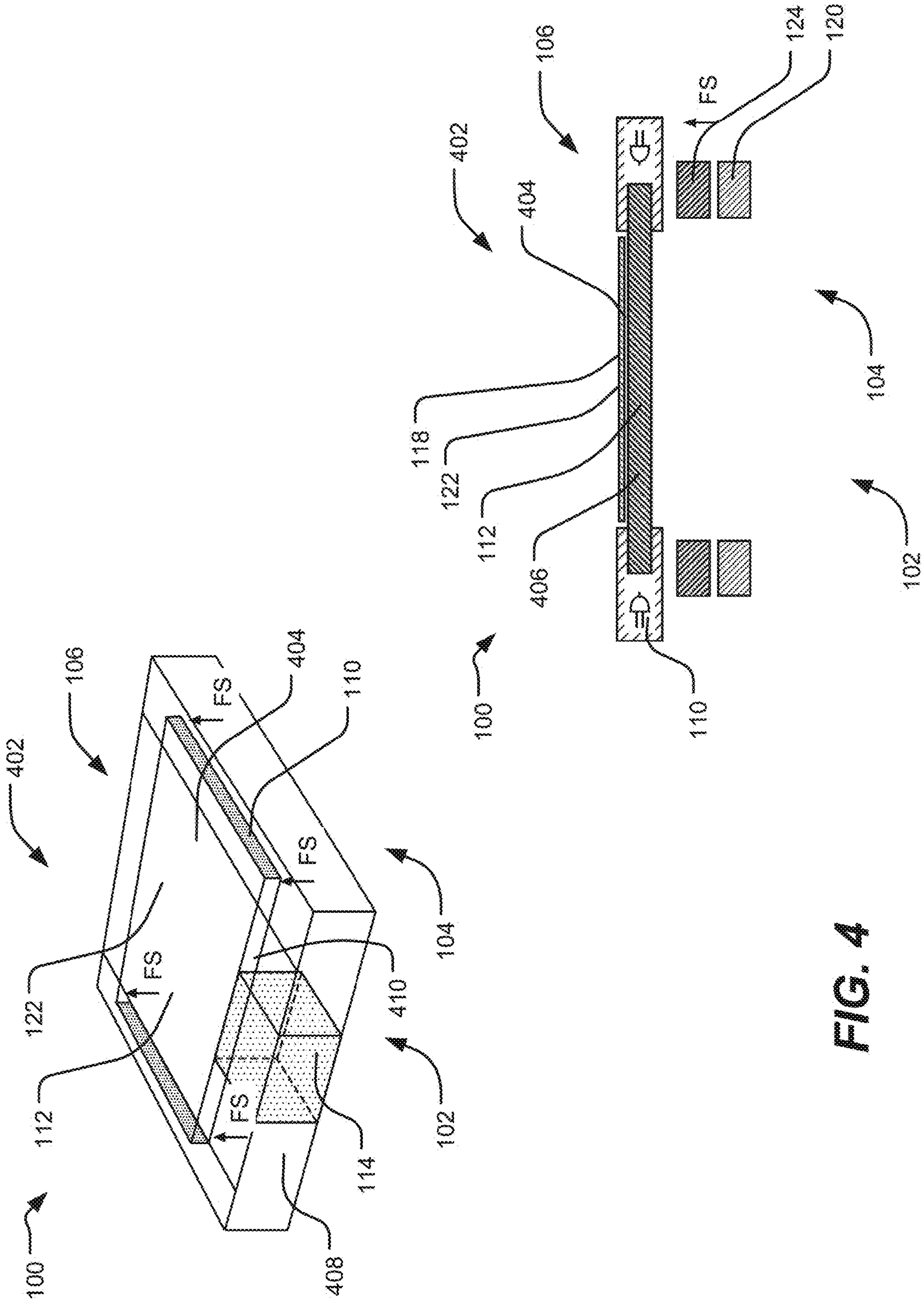
FIG. 4 illustrates an example system for characterizing a health parameter with a multi-signal scanning device having a standing platform form factor.

For instance, FIG. 4 depicts a large-scale device 402 using the multi-sensor arrangement to form a multi-detection signal standing scanning surface 404. For instance, the device can include a substantially planar and/or flat standing platform 406 defined by the glass portion 112. The camera 114 can be formed into a frame 408 around the glass portion 112, for instance, at a side surface 410 of the glass portion 112, or below the glass portion 112. The glass portion 112 can be disposed over and/or rest on one or more acoustic transducers 124 and/or one or more force sensors 120. The electrically conductive ink can be disposed at least partially on the contact surface 122 of the glass portion 112.

The multi-detection signal scanning devices 104 discussed herein can be used for humans, animals, plants for detecting disease and/or nutritional absorptions, and/or water content of leaves. Additionally, the different sensor components and assemblies disclosed herein can be modular and/or interchangeable for providing different combinations of cross-domain analysis of the different detection signal modalities. As such, different signal sensors and actuators can be removed and/or installed to change the functionality of the device for particular use cases.

Figure 5:
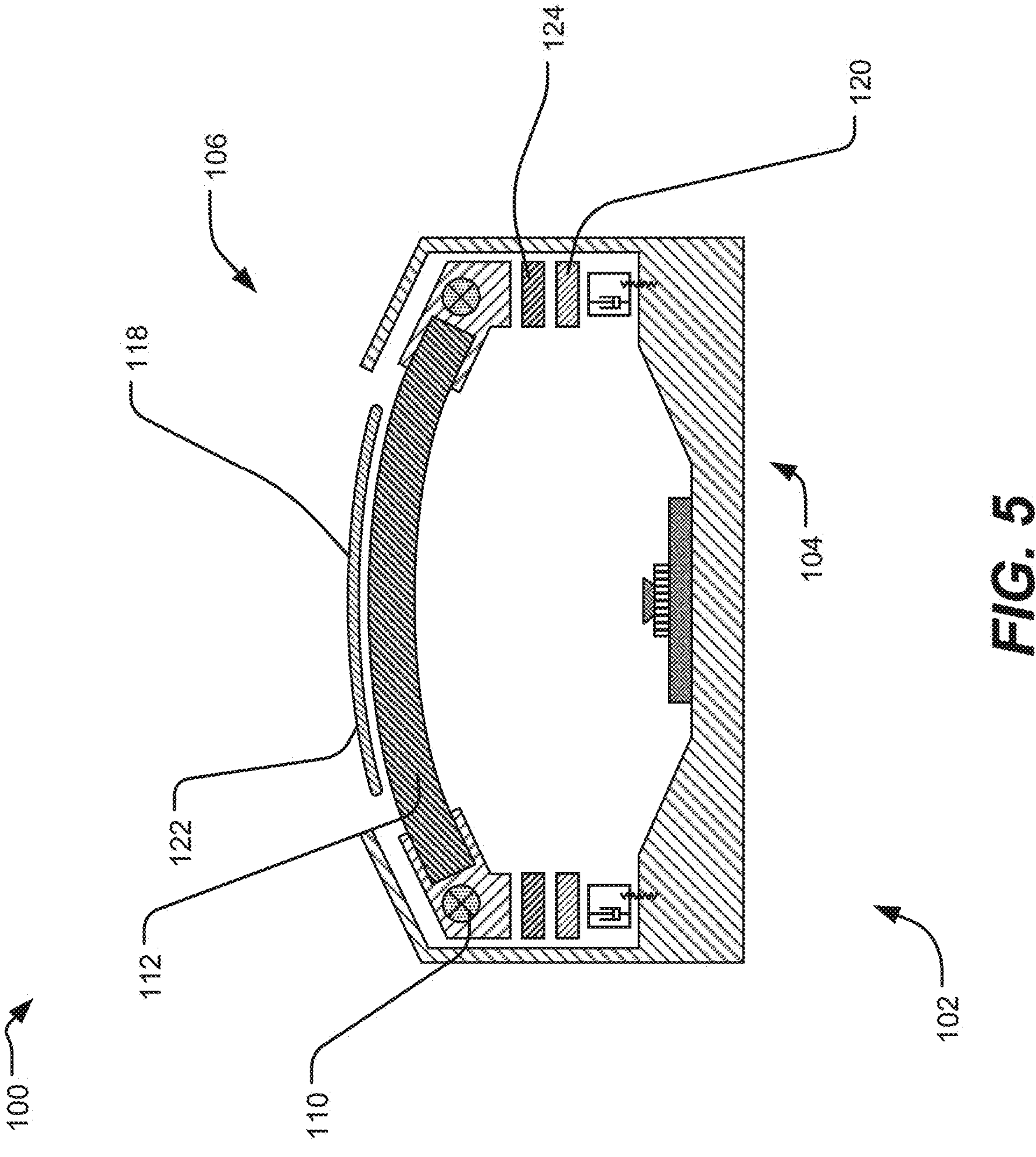
FIG. 5 depicts an example system for characterizing a health parameter with a multi-signal scanning device having various configurations of internal sensor components.

FIGS. 5-7D depict various examples of the multi-detection signal scanning device 104. As depicted in FIG. 5, the scanning portion 106 can include a cylindrical shaped multi-detection signal sensor (e.g., although the multi-detection signal sensor could be any shape) that has a glass surface 112. The glass surface 112 can be curved or not, and can trap electromagnetic waves in any range from UV to long range infrared. The resulting FTIR phenomena can create data that provides an understanding of the composition of the sample/object contacting the contact surface 122, and mechanical properties of the surface that the glass touch.

Additionally, acoustic transducers 124 can transmit acoustic waves through the glass portion 112 and out the contact surface 122 (e.g., omitting direct sample contact with the acoustic transducers due to the spacing of the glass portion 112). These acoustic transducers 124 can also connect to force sensors and/or a spring damper system to not only measure the force applied on the glass but also ensure good contact between the glass and the object. Contact force could be one of the detection signal modalities (e.g., a fifth detection signal modality). Moreover, the surface of the glass portion 112 can be painted or coated with conductive transparent ink in shape of one or several electrodes. Therefore, electrical signals could be both transmitted into the object contacting the contact surface 122 and/or read from the object. Moreover, thermal signals can be generated and/or detected using the optical sensor assembly (e.g., using infrared/ultraviolet LEDs), the acoustic sensor assembly, and/or the electrical sensor assembly.

Figure 6A:
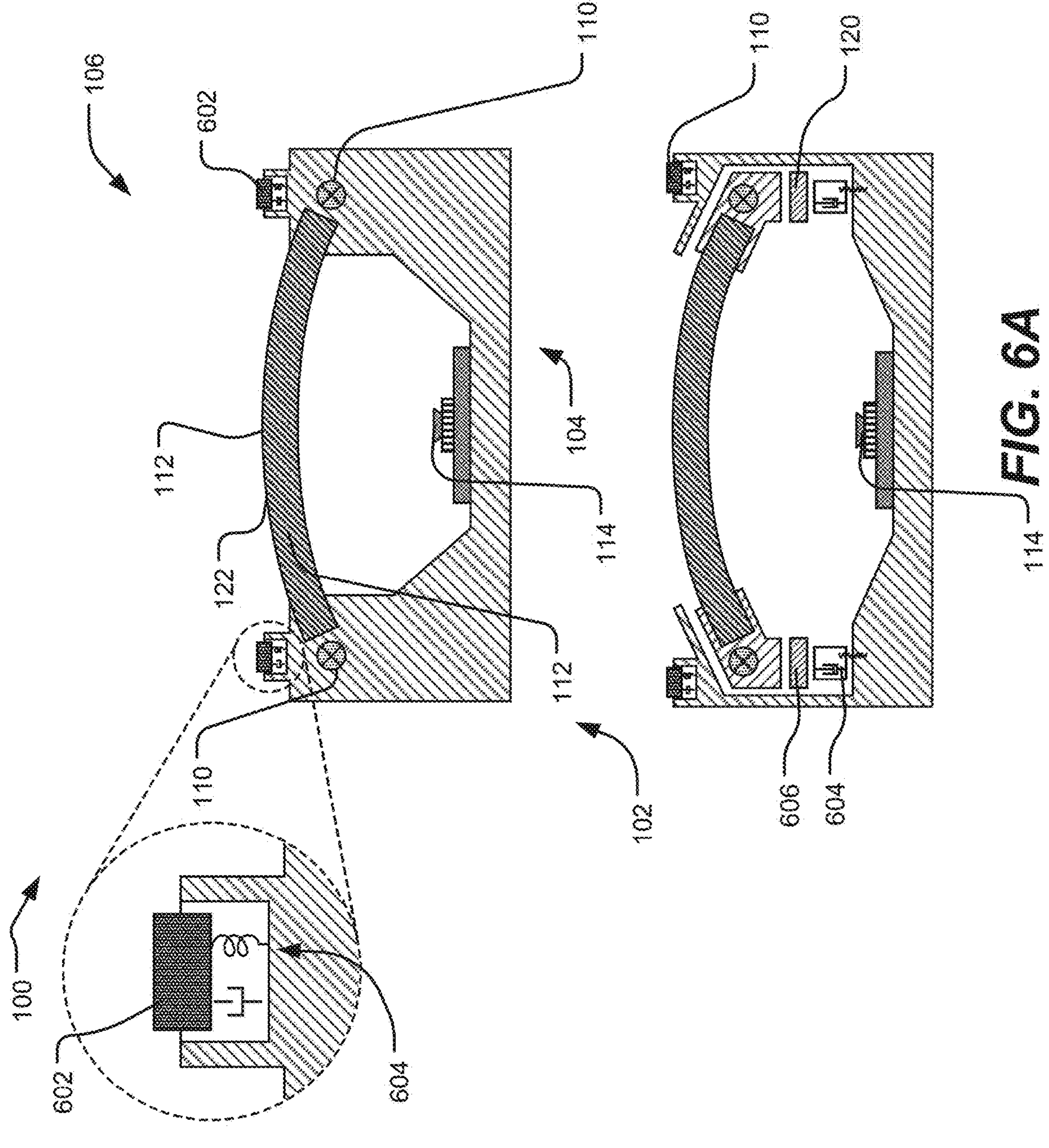
FIGS. 6A-6C depict example systems for characterizing a health parameter with a multi-signal scanning device having various configurations of internal sensor components.
Figure 6B:
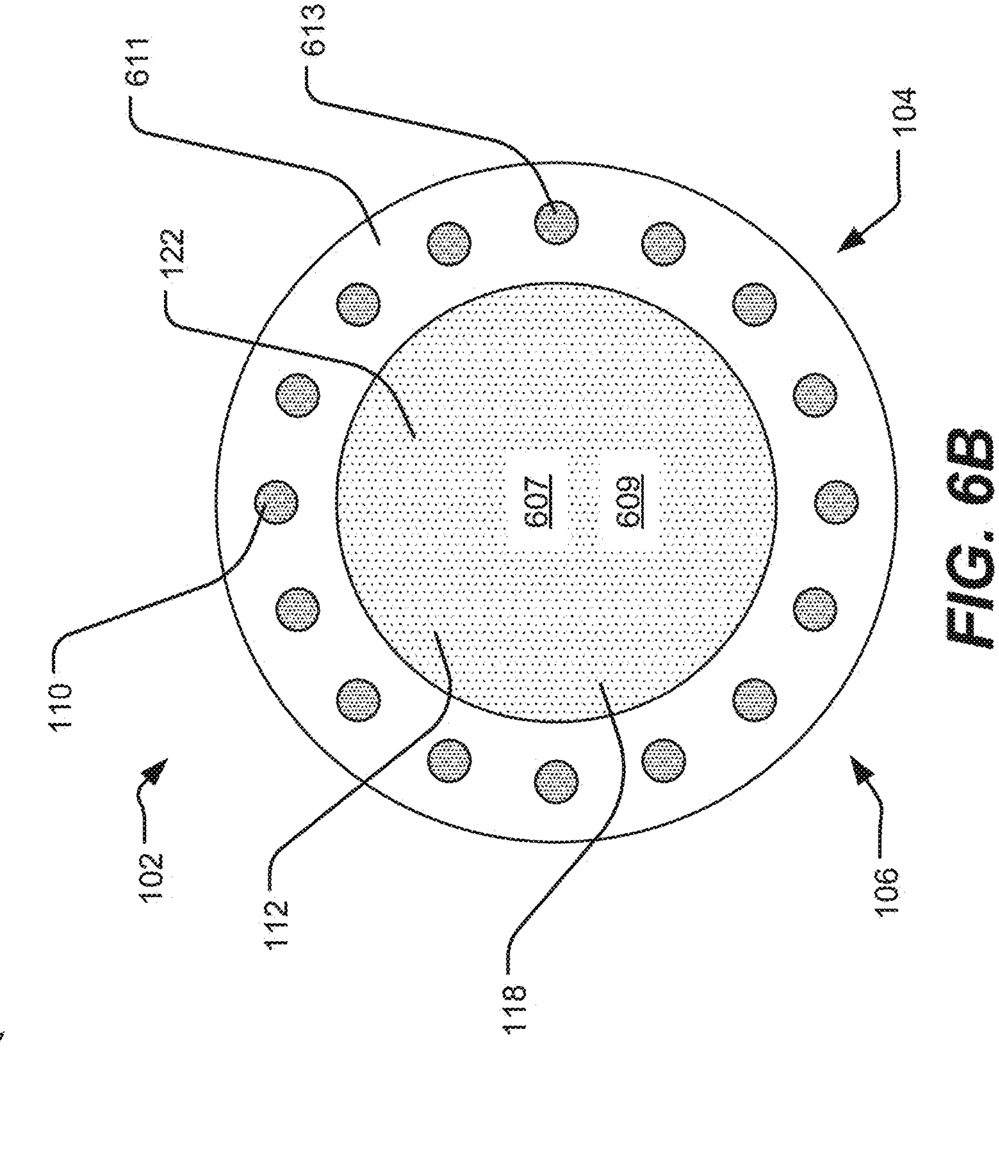

FIGS. 6A and 6B depict another example configuration of sensor assemblies of the multi-detection signal scanning device 104. In these examples, electrical and/or acoustic transducers 602 can be in direct contact with the contacting body. The electrical and/or acoustic transducers 602 can also work as electrical electrodes in this approach by having electrically conductive surfaces on one or more end(s) of the one or more acoustic transducers 124. The electrically conducting ink forming electrodes can be formed onto the one or more acoustic transducers 124 in addition to, or alternatively to, being disposed on the contact surface 122. The one or more acoustic transducers 124 can also be connected directly to spring damper systems 604 and/or force sensors 606 (e.g., disposed around an outer circumference/perimeter of the scanning portion 106). Additionally or alternatively, the glass or transparent surface can be connected to the force sensors and/or a spring damper system 604, for instance, positioned below a mounting frame which receives an outer end of the glass portion 112 and/or houses the one or more LEDs 110. As shown in FIG. 6B, the scanning portion 106 of the multi-detection signal scanning device 104 can include an inner portion 607 (e.g., the glass portion 112) covered fully or at least partly in electrically conductive ink 609 and an outer portion 611 including one or more one or more acoustic transducers 124 LED openings, force sensors 606, and/or electrical sensors 602 (e.g., forming an outer perimeter/outer circumference 613 to the contact surface of the inner portion 607.

Figure 6C:
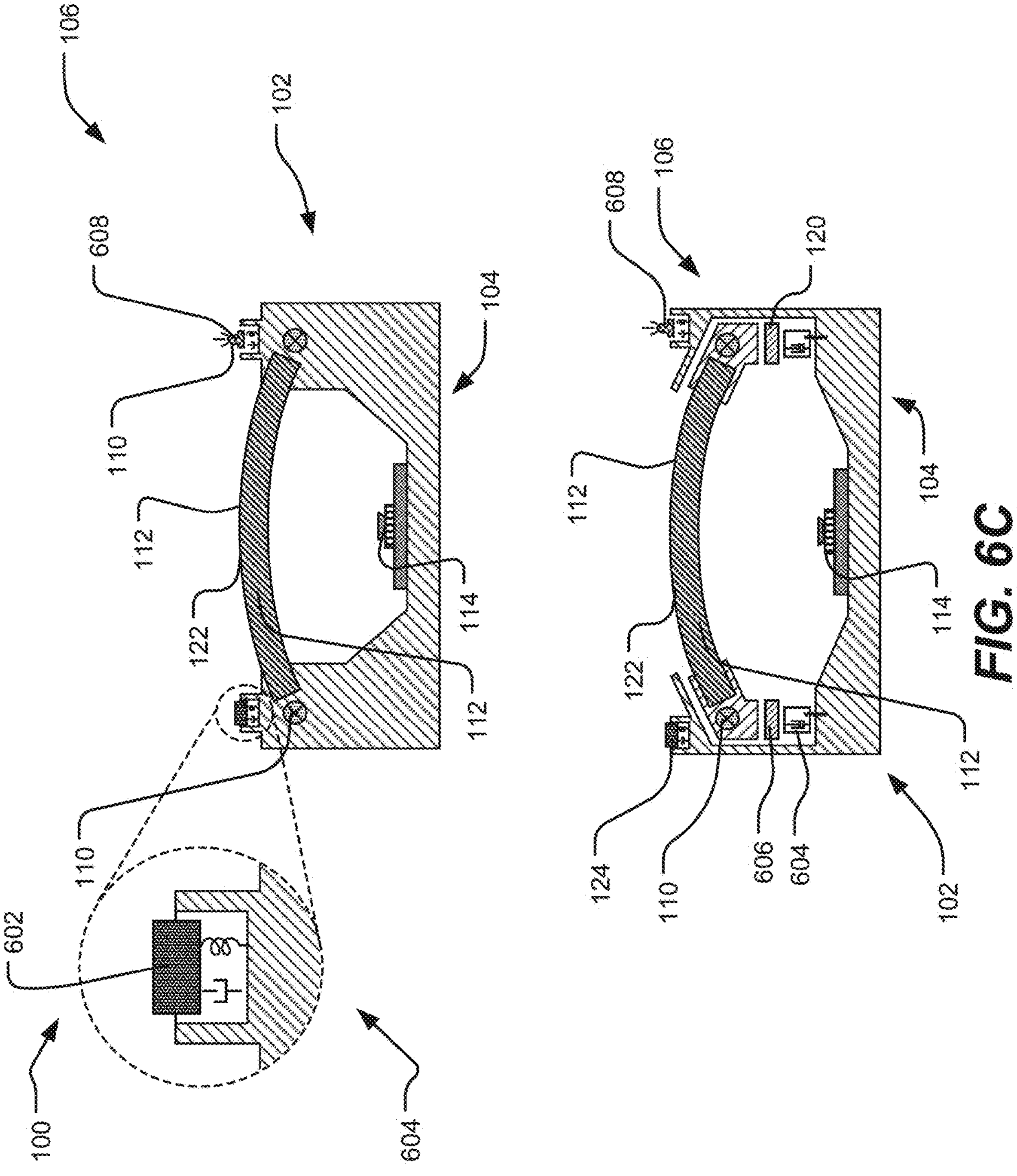

FIG. 6C depicts additional example configurations of the multi-detection signal scanning device 104. In this examples, EM emitter LEDs 608 can be in direct contact with the contacting body in addition or alternatively to the one or more acoustic transducers 124. The acoustic transducers 124 can also work as electrical electrodes in this approach by having electrically conductive surfaces. Moreover, because the LEDs 608 forming the outer circumference/perimeter of the scanning portion 106 can be infrared lights, they could be used to thermally stimulate the contacting body. This can be performed in addition to the electrical electrodes printed or painted on the glass. As discussed above, the one or more acoustic transducers 124 can be connected to the spring damper systems 604 and/or force sensor assembly 606. The glass portion 112 and/or transparent surface 111 can also be connected to the force sensors 606 and/or spring damper system 604.

Figure 7A:
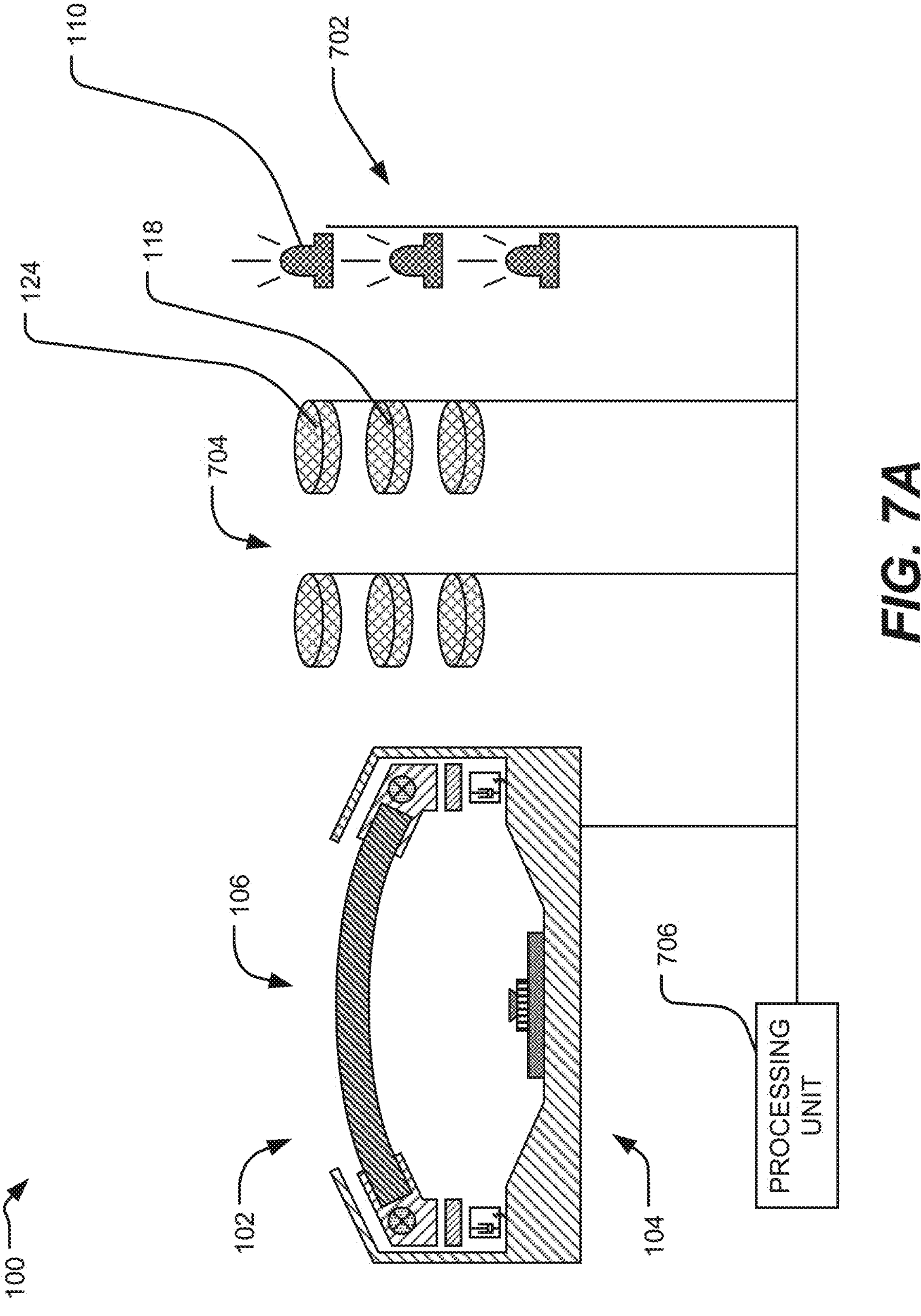
FIGS. 7A-7D depict an example system for characterizing a health parameter with a multi-signal scanning device having various configurations of internal sensor components and external sensor/actuation components.
Figure 7B:
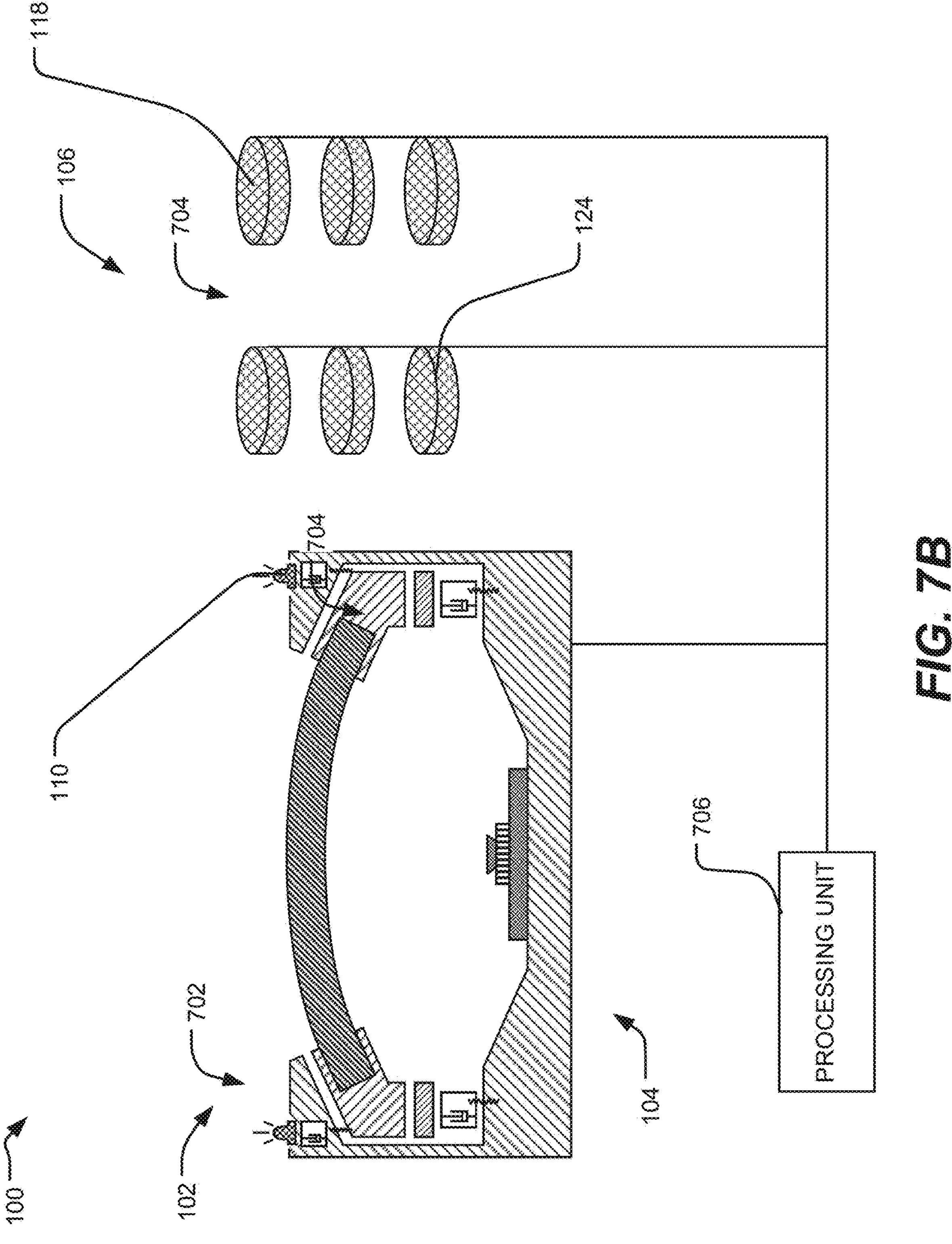
Figures 7C, 7D:
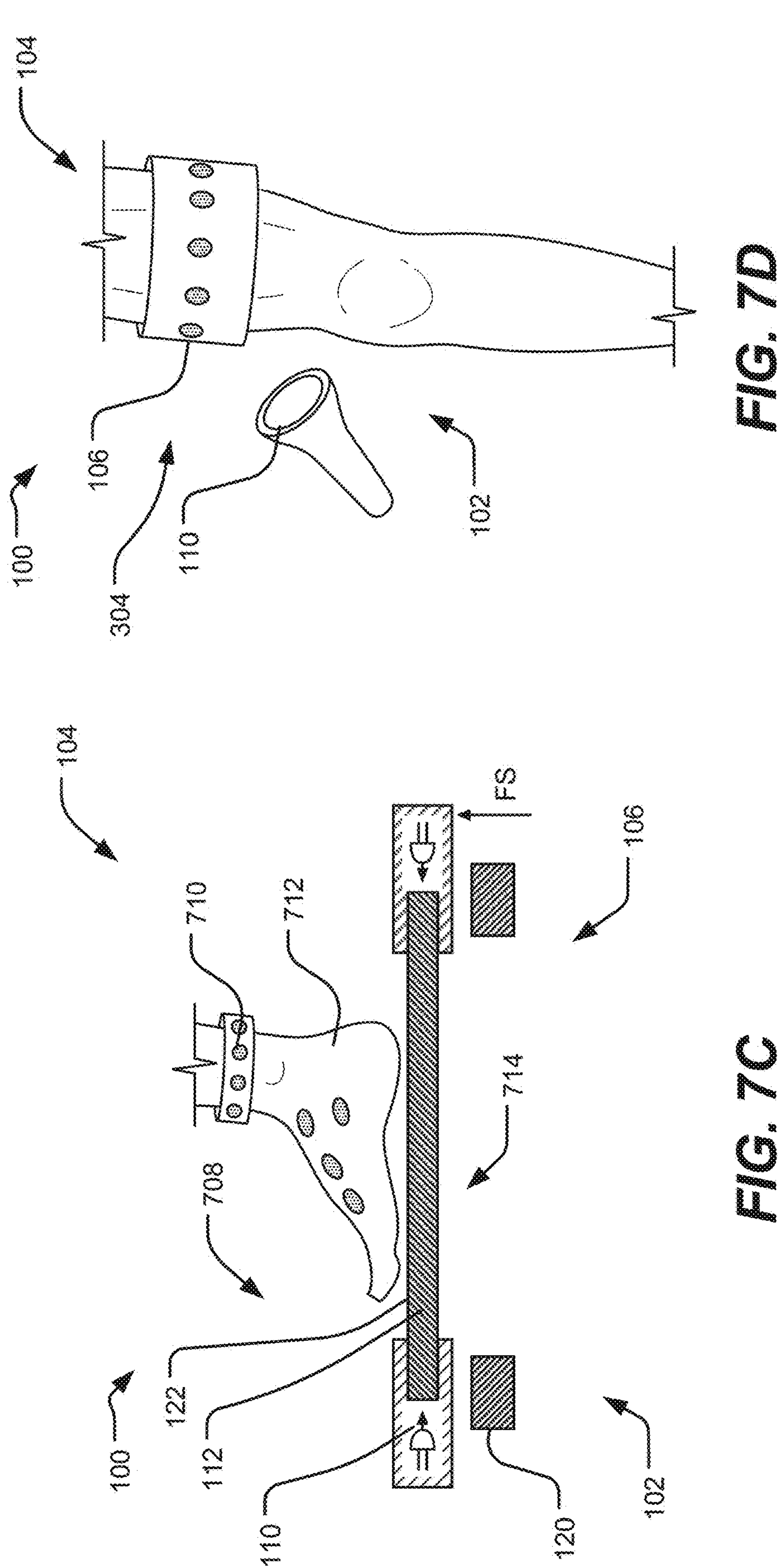

FIGS. 7A-7D depict examples of the sensor device 102 in which the optoelectrical portion 702 is separated from the acoustoelectric 704 portion. However, in these configuration(s) the sensors/transducers can still be communicatively connected to each other via a processing unit 706 of the analytics platform. For example, components of the optical sensor assembly (e.g., EM emitter, at least some or all of the LEDs 110) can be external, as shown in FIG. 7A, or placed around the glass surface 112, as shown in FIG. 7B. One could also use, as shown in FIGS. 7C and 7D, a large scale device 708 that works in connection with the electroacoustic wearables 710 and/or sensors for analyzing a human foot 712. An example of the application could be a standing platform 714 for analyzing a diabetic foot and wounds or foot perfusion (e.g., or hand characteristics) via simultaneous stimulation of cells with acoustic waves, while also analyzing their optical and electrical behavior (e.g., as shown in FIG. 7C). In another example, the optical portion could be designed into a probe or cuff 304 (e.g., as shown in FIG. 7D) that analyzes human body parts (e.g., arm, legs, toros, etc.) or plants while external electroacoustic sensor/transduces are used to analyze and/or stimulate the target sample area. One example could be analysis of the vascular system (e.g., via acoustic signals, force signals, electrical signals, and/or optical signals) while the body is subjected to electrical stimulation.

Figure 8:
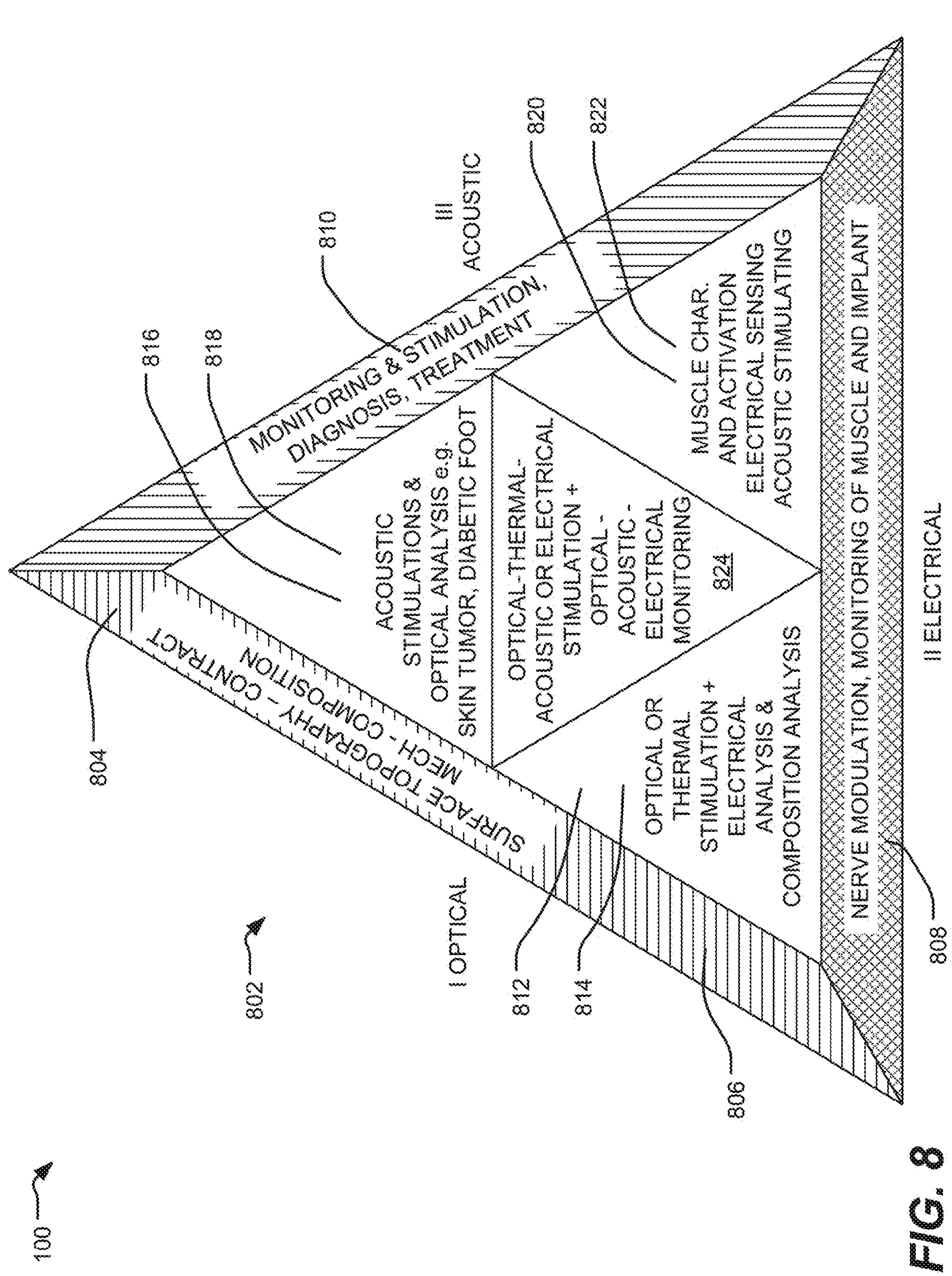
FIG. 8 depicts an example diagram of multi-signal analysis techniques used by a system for characterizing a health parameter with a multi-signal scanning device.

FIG. 8 depicts an example diagram 802 of multi-signal analysis techniques 804 that can be used by any of the system disclosed herein. The diagram of FIG. 8 shows how different combinations of signal can be used for different sensing and analytics procedures. For example, FIG. 8 shows how three or four different signal types (e.g., optical 806, electrical 808, acoustic 810, and/or thermal) can be integrated into a cross-domain analysis. For example, optical sensing/actuating modality 806 can be used for determining a surface topology, contact mechanics of the surface (e.g., friction, roughness, slippage), and/or surface composition. The electrical sensing/actuating modality 808 can be used for nerve modulation, monitoring of muscle activity, and/or detecting implant characteristics. The acoustic sensing/actuating modality 810 can include monitoring or stimulation of muscle, bone, and/or tendon tissue, blood flow, combinations thereof, and/or diagnosis/treatments. When combined into a two-signal cross-domain analysis, the optical sensing/actuating modality can combine with the electrical sensing/actuating modality to perform optical or thermal stimulations 812 with electrical analysis and/or composition analysis 814. When combined into a two-signal cross-domain analysis, the optical sensing/actuating modality 806 can combine with the acoustic sensing/actuating modality 810 to perform acoustic stimulations 816 with optical analysis 818 (e.g., for skin tumor analysis, diabetic foot analysis, etc.). When combined into a two-signal cross-domain analysis, the acoustic 810 sensing/actuating modality can combine with the electrical sensing/actuating modality 808 to perform muscle characterization and activation 820 with electrical sensing and/or acoustic stimulation 822. When combined into a three or four-signal cross-domain analysis 824, the optical, electrical, acoustic, and/or thermal sensing/actuating modularities can be combined for optical-thermal-acoustic and/or electrical stimulation with optical-acoustic-electrical and/or thermal monitoring, which can be used to inform any of the functionalities discussed herein. Accordingly, in some examples, the LEDs 110 and/or the electromagnetic wave emitter can emit light directly onto the surface of the body and then the optical signals can be read with the light sensor (e.g., the camera 114) and can be enhanced and/or modified with the electrical or acoustic emitters, or, vice versa, the electromagnetic waves or thermal energy from the LEDs 100 can influence the acoustic signals and/or the electrical signals.

FIG. 9 depicts an example method 900 for characterizing a health parameter using multiple sensor types, such as the multi-sensor scanning device 102. The method 900 can be performed by any of the systems disclosed in FIGS. 1-8.

In some examples, at operation 902, the method 900 can collect a first type of data using a first sensor assembly, the first sensor assembly having: a glass section forming a contact surface; one or more LEDs operable to provide electromagnetic waves to an interior of the glass section; and a light sensor directed at the glass section, the light sensor operable to detect scattered light transmitting through the glass section caused by frustrated total internal reflection (FTIR) occurring at the contact surface. At operation 904, the method 900 can collect a second type of data using a second sensor assembly, the second sensor assembly having one or more electrical sensors or one or more electrical actuators. At operation 906, the method 900 can collect a third type of data using a third sensor assembly, the third sensor assembly having one or more acoustic sensors or one or more acoustic actuators. At operation 908, the method 900 can generate a health parameter characterization using at least two of the first type of data, the second type of data, or the third type of data. At operation 910, the method 900 can cause a display to present a visual indication of the health parameter characterization.

It is to be understood that the specific order or hierarchy of steps in the method(s) depicted throughout this disclosure are instances of example approaches and can be rearranged while remaining within the disclosed subject matter. For instance, any of the operations depicted throughout this disclosure may be omitted, repeated, performed in parallel, performed in a different order, and/or combined with any other of the operations depicted throughout this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A multi-sensor scanning device for characterizing a health parameter, the multi-sensor scanning device comprising:
- a scanning portion formed at an end of the multi-sensor scanning device, the scanning portion including:
  - a first sensor assembly having:
    - a glass section forming a contact surface;
    - one or more light emitting diodes (LED) s operable to provide electromagnetic waves to an interior of the glass section; and
    - a light sensor directed at a transmission surface of the glass section;
  - a second sensor assembly including one or more sensors directed at a same target area as the contact surface, the one or more sensors being a different type of sensor than the first sensor assembly; and
    - a transparent, electrically conductive ink or coating disposed on the contact surface; and
- a mounting portion at least partially housing one or more components of the scanning portion.

2. The device of claim 1, further comprising: wherein,
- the one or more sensors of the second sensor assembly include one or more electrical transducers disposed at least partly around the contact surface.

3. The device of claim 2, wherein,
- the one or more sensors of the second sensor assembly include one or more acoustic actuators or one or more acoustic sensors disposed at least partly around the contact surface.

4. The device of claim 1, wherein,
- the one or more sensors of the second sensor assembly include one or more force sensors communicatively coupled to the glass section such that the one or more force sensors are operable to detect a force applied to the contact surface of the glass section.

5. The device of claim 1, further comprising:
- a spring-loaded dampening system at the scanning portion of the multi-sensor scanning device.

6. The device of claim 1, wherein,
- the light sensor is operable to detect scattered light, originating from the one or more LEDs, scattered by frustrated total internal reflection (FTIR) occurring at the contact surface.

7. The device of claim 1, wherein,
- the multi-sensor scanning device is a handheld device; and
- the mounting portion includes a handle portion of the handheld device.

8. The device of claim 1, wherein,
- the multi-sensor scanning device is a standing platform; and
- the mounting portion includes a base of the standing platform.

9. The device of claim 6, wherein,
- the multi-sensor scanning device is a wearable device; and
- the mounting portion includes a strap of the wearable device.

10. A system for characterizing a health parameter using multiple sensor types, the system comprising:
- a scanning portion formed at an end of a scanning device, the scanning portion including:
  - a first sensor assembly having:
    - a transparent section forming a contact surface;
    - one or more electromagnetic wave emitters operable to provide electromagnetic waves to an interior of the transparent section; and
    - a light sensor, and/or camera directed at the transparent section, the light sensor, and/or the camera being operable to detect scattered light transmitting through the transparent section caused by frustrated total internal reflection (FTIR) occurring at the contact surface; and
- a second sensor assembly including one or more electrical sensors directed at a same target area as the contact surface, the one or more electrical sensors include:

an electrical signal emitter to provide electrical stimulation, and an electrical signal detector.

11. The system of claim 10, wherein, the one or more electrical sensors includes at least one of:

a transparent, electrically conductive ink disposed on the contact surface; or one or more electrodes disposed at least partly around the contact surface.

12. The system of claim 10, wherein, the light sensor is a visible light camera.

13. The system of claim 10, wherein, the second sensor assembly is integrally formed into the scanning portion of the scanning device.

14. The system of claim 10, wherein, the second sensor assembly is a remote sensor assembly separate from the scanning portion of the scanning device.

15. The system of claim 14, wherein, the second sensor assembly includes a wearable device.

16. The system of claim 15, wherein, the wearable device includes a third sensor assembly having at least one of an acoustic actuator or an acoustic sensor.

17. The system of claim 10, further comprising:

a third sensor assembly including one or more acoustic actuators, or one or more acoustic transducers, directed in the same target area as the contact surface.

18. A method for characterizing a health parameter using multiple sensor types, the method comprising:

collecting a first type of data using a first sensor assembly, the first sensor assembly having:

a glass section forming a contact surface;

one or more LEDs operable to provide electromagnetic waves to an interior of the glass section, the electromagnetic waves being infrared or ultraviolet; and a light sensor directed at the glass section, the light sensor operable to detect scattered light transmitting through the glass section caused by frustrated total internal reflection (FTIR) occurring at the contact surface;

collecting a second type of data using a second sensor assembly, the second sensor assembly having one or more electrical sensors or one or more electrical actuators;

collecting a third type of data using a third sensor assembly, the third sensor assembly having one or more acoustic sensors or one or more acoustic actuators;

generating a health parameter characterization using at least two of the first type of data, the second type of data, or the third type of data; and causing a display to present a visual indication of the health parameter characterization.

19. The method of claim 18, wherein, the first sensor assembly, the second sensor assembly, and the third sensor assembly are formed into a scanning portion of a handheld scanning device.

* * * * *